United States Patent [19]

Farzin-Nia et al.

[11] Patent Number: 5,106,302

[45] Date of Patent: Apr. 21, 1992

[54] METHOD OF FRACTURING INTERFACES WITH AN ULTRASONIC TOOL

[75] Inventors: Farrokh Farzin-Nia, Inglewood, Calif.; Rohit C. L. Sachdeva, Plano, Tex.; Howard M. Alliger, Millville, N.Y.

[73] Assignee: Ormco Corporation, Glendora, Calif.

[21] Appl. No.: 588,281

[22] Filed: Sep. 26, 1990

[51] Int. Cl.⁵ .......................... A61C 5/00; A61C 3/00; A61C 1/07; A61C 3/03

[52] U.S. Cl. ........................................ 433/215; 433/3; 433/24; 433/119

[58] Field of Search ................... 433/3, 24, 118, 119, 433/4, 159, 215

[56] References Cited

U.S. PATENT DOCUMENTS

| | | | |
|---|---|---|---|
| 2,947,082 | 8/1960 | Epstein | 433/119 |
| 3,332,150 | 7/1967 | Mumaw | 433/24 |
| 3,526,219 | 9/1970 | Batamuth | 433/119 |
| 3,924,335 | 12/1975 | Balamuth et al. | 433/119 |
| 4,169,984 | 10/1979 | Parisi | 310/323 |
| 4,281,987 | 8/1981 | Kleesattel | 433/103 |
| 4,406,284 | 9/1983 | Banko | 128/303 |
| 4,608,019 | 8/1986 | Kumgle et al. | 433/178 |
| 4,773,855 | 9/1988 | Levy | 433/102 |
| 4,824,366 | 4/1989 | Hohmann et al. | 433/32 |
| 4,907,965 | 3/1990 | Martin | 433/3 |

OTHER PUBLICATIONS

Comparisons of Different Debonding Techniques for Ceramic Brackets: An In Vitro Study, Samir E. Biskara, DDS, BDS, D. Ortho., MS* and Timothy S. Trulove, DDS, MS**, Iowa City, Iowa and Montgomery, Ala., Aug. 1990.

*Primary Examiner*—John J. Wilson
*Assistant Examiner*—Cindy A. Cherichetti
*Attorney, Agent, or Firm*—Wood, Herron & Evans

[57] ABSTRACT

Method for fracturing the interface between dental structures that have been secured together. The device comprises an ultrasonic tool for providing bi-directional movement of a preferred amplitude and frequency. The tool is applied against one of the dental structures at an acute angle with respect to a plane in which the interface between the dental structures lies.

5 Claims, 3 Drawing Sheets

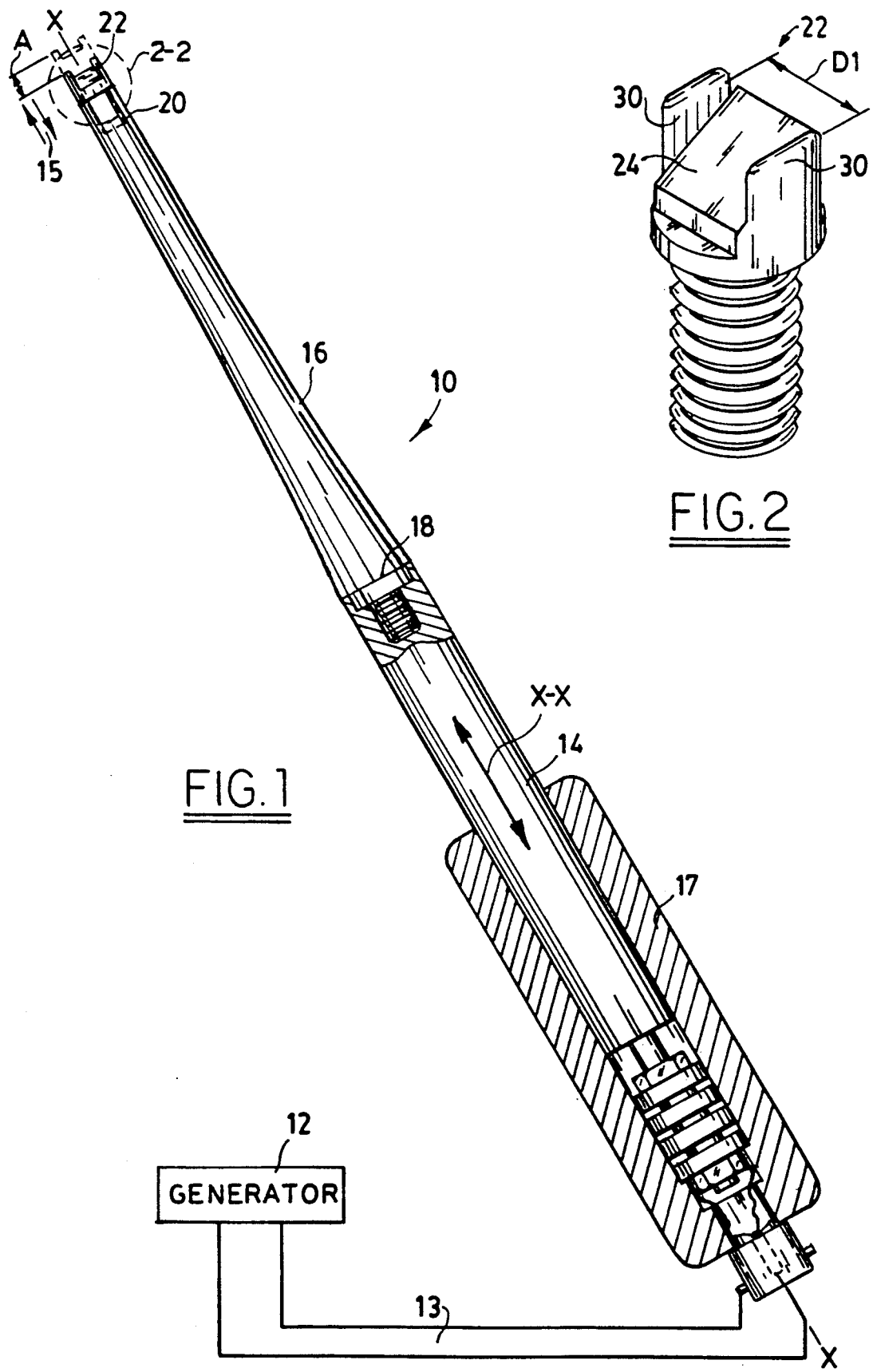

METHOD OF FRACTURING INTERFACES WITH AN ULTRASONIC TOOL

The present invention relates to a dental tool and method of use, and more particularly, to a tool for fracturing the interface between two dental structures that have been secured together.

BACKGROUND OF THE PRESENT INVENTION

In the dental and orthodontic field it is often necessary to break an adhesive bond that has been formed between two dental structures. For example, the removing of orthodontic bands or brackets from teeth at the completion of treatment. Typically, orthodontic brackets are removed by mechanical devices with the application of a force. These devices generally comprise various types of orthodontic pliers or mechanical arms that can be used as levers. Orthodontic bracket removing instruments generally apply force to the interface between the bracket and the tooth that contains an appropriate orthodontic adhesive. In the situation of typical metal orthodontic brackets, the force that is applied deforms the orthodontic bracket which is substantially more ductile than the tooth or adhesive. Deformation of the bracket creates microcracks on and within the adhesive layer which ultimately results in bond failure. While such techniques have been generally accepted in removing metal orthodontic brackets, the debonding of ceramic brackets (for example, brackets made of alumina) is not easy to accomplish. This is due in part to the high rigidity of the ceramic materials used to form the bracket, thus deformation of the ceramic bracket does not occur. Therefore, the force needed to debond a ceramic bracket is substantially greater since tensile or shear mode of failure must occur as opposed to the peeling type of removal that occurs in metal type brackets. Additionally, ceramic brackets frequently use a chemical bonding system which provides extremely high bond strengths. The typical forces used to debond ceramic brackets can lead to substantial trauma to the patient, as well as the possibility of removing enamel from the tooth which is highly undesirable.

Several methods have been suggested in the prior art in order to minimize enamel damage and patient trauma during debonding of such brackets. One such method includes the application of heat to soften the adhesive. An example of this is illustrated in U.S. Pat. No. 4,907,965. Another method is a thorough cleaning of the bracket base periphery by dental burrs prior to debonding. Yet a third method requires use of a lever arm for applying a tortional load to the bracket. However, none of these proposed methods have been successful in either reducing patient trauma and/or reducing the possibility of enamel damage.

There has also been suggested in the prior art the removing of orthodontic brackets through ultrasonic devices of the magneto-restrictive type. However, such devices are not very efficient as they require the application of the ultrasonic tool for time periods upwards of 30 to 40 seconds per bracket. This is a substantial amount of time for the orthodontist to remove a bracket which generally results in substantial patient trauma and discomfort.

The present invention provides an improved orthodontic tool and method for fracturing the bond between two dental structures that is quick and does not cause any significant trauma to the patient.

SUMMARY OF THE INVENTION

In one aspect of the present invention, there is provided a dental tool for fracturing the interface between two dental structures that have been secured together. The tool includes a generator for providing power at a predetermined frequency and a converter for producing a bi-directional movement along the axis of the converter at said predetermined frequency. A horn is secured to the converter having an outer working end for transferring said bi-directional movement to one of said dental structures so as to fracture the interface between said dental structures.

In another aspect of the present invention, there is provided a method for fracturing the interface between two dental structures that have been secured together. The method includes providing an ultrasonic tool having a generator for providing a predetermined frequency, a converter for producing a bi-directional movement along the axis of the converter and a horn having a outer working end for transferring said bi-directional movement to one of said dental structures. The method further includes the step of placing the outer working end of the horn at an acute angle with respect to the interface between said dental structures.

DESCRIPTION OF THE DRAWINGS

FIG. 1 is a perspective view of a dental tool made in accordance with the present invention;

FIG. 2 is a perspective view of the tip of the the ultrasonic tool of FIG. 1 shown within line 2—2;

DETAILED DESCRIPTION OF THE PREFERRED EMBODIMENT

Figure 3:
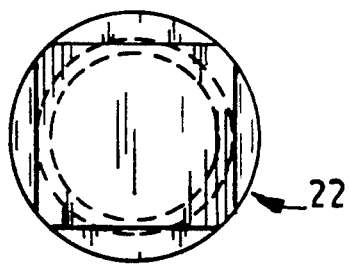
FIG. 3 is a top plan view of the tip of FIG. 2.
Figure 4:
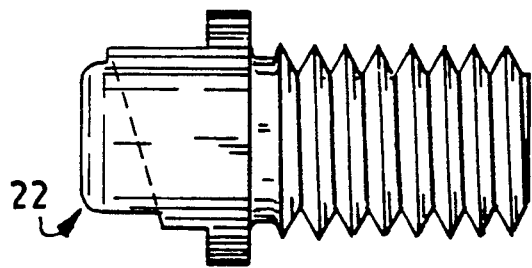
FIG. 4 is a side elevational view of the tip of FIG. 2.
Figure 5:
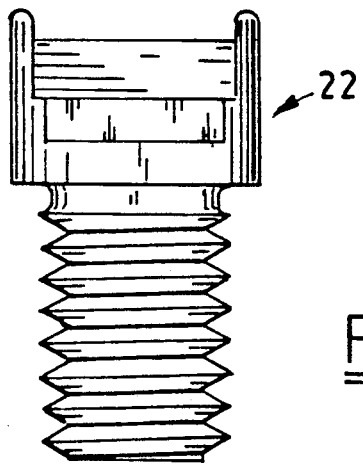
FIG. 5 is a front elevational view of the tip of FIG. 2.
Figure 6:
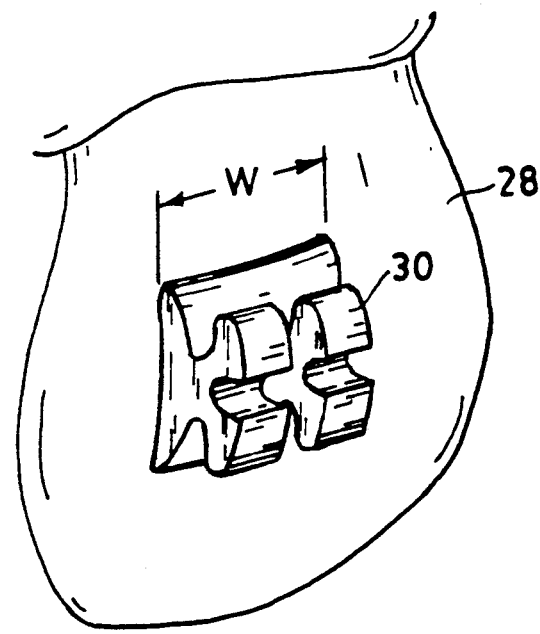
FIG. 6 is an enlarged perspective view of an orthodontic bracket secured to a tooth upon which the tool of FIG. 1 is to be used.

Referring to the Figures there is illustrated an ultrasonic dental tool 10 made in accordance with the present invention. The tool 10 is designed to be electrically connected to an oscillation generator 12 by an appropriate power cable 13 which is used to produce a predetermined electrical frequency. The oscillation generator 12 is a conventional generator as is well known in the prior art. Preferably, the generator 12 provides an ultrasonic frequency equal to or greater than about 18 kHz. In the particular embodiment illustrated the generator 12 is used to provide a frequency of about 40 kHz.

The dental tool 10 comprises a converter 14 for producing a bi-directional movement along the longitudinal axis X—X of the converter 14 as illustrated by arrows 15. The converter 14 is made of a piezoelectric material such that movement is substantially directional along the longitudinal axis X—X of the converter. It is essential to use a converter which provides substantially only bi-directional movement to minimize the radial vibration of the tip and thus provide substantially only bi-directional movement along a X—X axis. For the purpose of the present invention, a bi-directional movement shall mean a forward and backward motion along a single axis. Preferably, the lateral movement at the tip is no greater than about 0.010 inches. (0.254 mm) during use of the device. Magneto-restrictive devices of the prior art, due to the nature of their construction, produce relatively large amounts of radial vibration (often referred to as lateral) which generates heat and does not have a positive function in fracturing the interface (the bond) between the tooth and bracket.

A horn 16 has a connecting end 18 which is secured to the converter 14 in any conventional manner and an outer working end 20 which is designed to provide physical movement along the X—X axis. In the particular embodiment illustrated horn 16 is secured to converter 14 by external threads formed on a projection which is received in a threaded opening in converter 14. Typically the horn 16 is designed to have a shape, configuration and mass so as to provide the desired amount of movement at its outer working end 20. A working tip 22 is secured at the outer working end 20 of horn 16. In the particular embodiment illustrated, tip 22 is secured to horn 16 by external threads 23 provided on the shank portion 25 which mate with internal threads provided in opening 27 in outer working end 20. It is to be understood that tip 22 may be secured to horn 16 in any desired manner appropriate for such devices. The horn 16 tapers down to a relatively narrow cylindrical tip having a diameter D of approximately 0.2 inches (5.08 mm). Preferably, the horn 16 is made of one of the following materials: titanium, aluminum, titanium alloys, or aluminum alloys. In the particular embodiment illustrated, the horn is made of a titanium alloy. However, it is to be understood that the horn 16 may be made out of any suitable material for use in an ultrasonic tool of the present invention.

A hand gripping handle 17 is secured to converter 14 and horn 16, preferably at a nodal point. In the particular embodiment illustrated handle 17 is an annular sleeve type structure made of aluminum. However, handle 17 may take any desired configuration and made of any desired material.

Referring to FIGS. 2-5 the working tip 22 is shown in greater detail. The tip 22 has an engaging surface 24 which is designed to be placed against the work piece for transmitting of the ultrasonic displacement to the work piece. In the particular embodiment illustrated, the ultrasonic tool is being used to debond an orthodontic bracket 26 from a tooth 28 of a patient. Preferably, as illustrated, the working tip 22 is designed so as to receive the bracket 26 and minimize the potential slipping off. In the particular embodiment illustrated, the working tip 22 is provided with a pair of space projections 30 disposed on two opposed sides of the engaging surface 24 so as to provide a receiving area there between. Preferably, as illustrated, the projections 30 are spaced apart a distance D1 which is slightly greater than the width W of the orthodontic bracket 26 which is to be received therebetween. This will assist in preventing the tool from moving off the orthodontic bracket due to the vibration of the tool. The tool 10 is designed such that the amplitude of movement A of the tip 22 at the outer working end of horn 20 is greater than 0.0005" (0.0127 mm). Preferably the amplitude A of the tip 22 is in the range of 0.001" (0.0254 mm) to approximately 0.005" (0.127 mm). The tip 22 is preferably made of a material having high abrasion resistance. The tip 22 can be made of Ti, Al, Ti alloys, Al alloys or stainless steels. Alternatively tip 22 may be coated with a high abrasion resistant material.

In the preferred form of the present invention a tracking system is provided in the generator to monitor the frequency and load being applied to the tip of the ultrasonic tool 10. The tracking system monitors the frequency and identifies the load and recalibrates the frequency of the generator so as to provide a resonance frequency to provide optimum power to the tip and substantially constant amplitude movement at the tip 22. This minimizes the possibility of the tip 22 simply stopping due to the amount of load being applied by the user.

Figure 7:
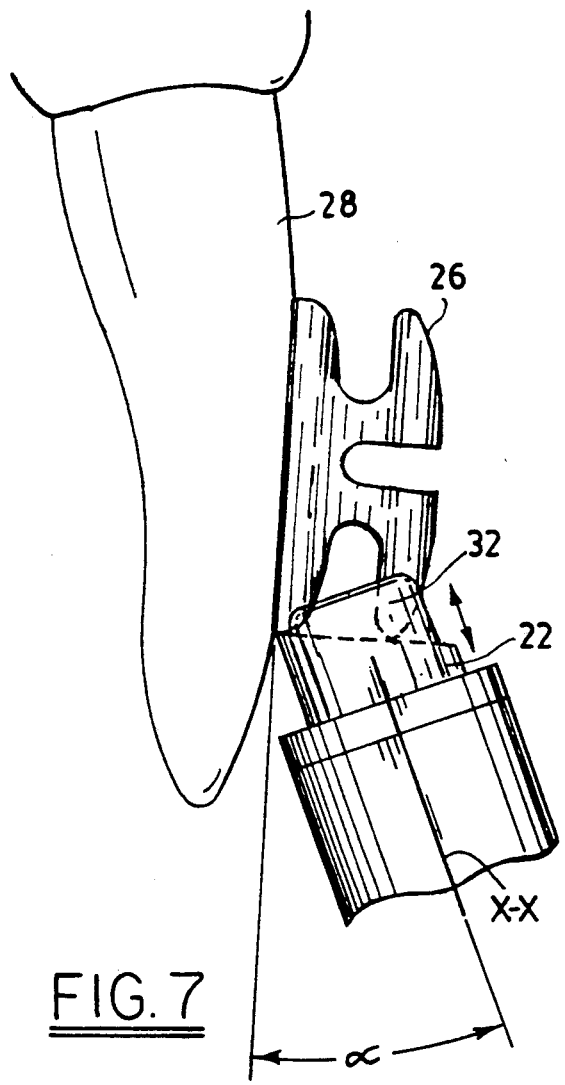
FIG. 7 is an enlarged partial side view of the tip area of the tool of FIG. 1 as applied against an orthodontic bracket which is secured to a tooth from which it is to be removed.
Figure 8:
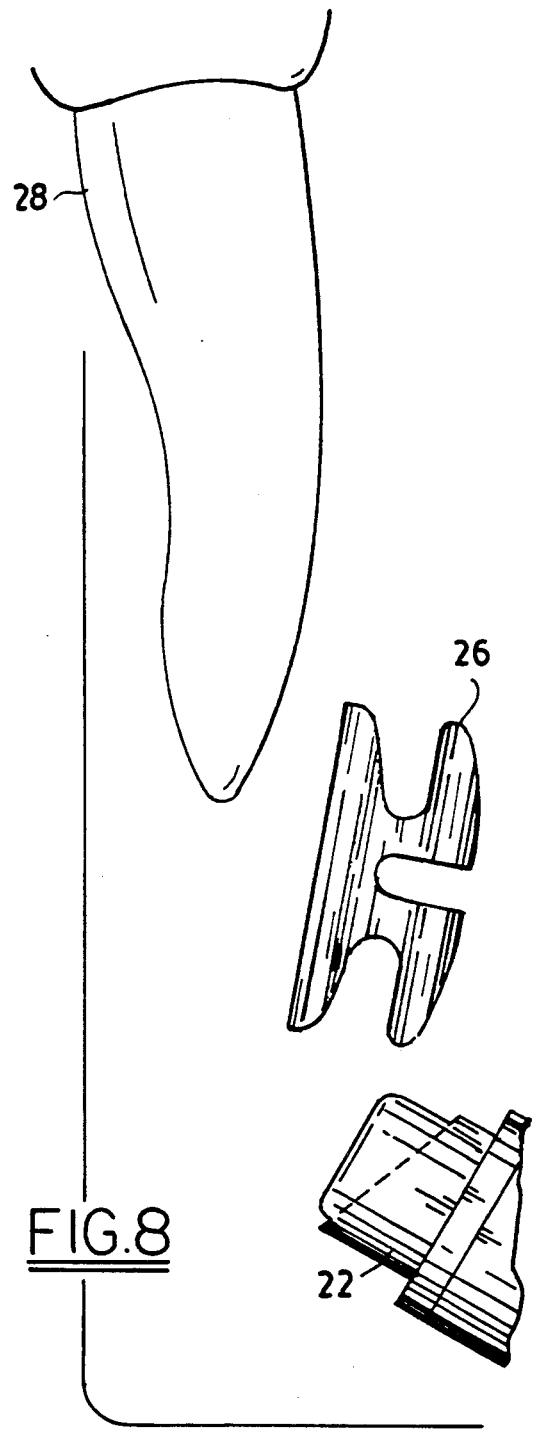
FIG. 8 is a view similar to FIG. 7 illustrating the orthodontic bracket removed from the tooth.

In order to more fully understand the operation of the device, an explanation as to its use will now be set forth In order to remove an orthodontic bracket 26 which is secured to a tooth 28 by an appropriate orthodontic adhesive, the tip 22 of the tool 10 is placed against the bracket 26 as illustrated in FIG. 7. The engaging surface 24 is designed to transfer the ultrasonic energy to one of the dental structures to be separated and not between the dental structures The ultrasonic energy is transferred through bracket 26 to the adhesive between the tooth and bracket. It is believed that the adhesive layer, due to its relatively low modulus of elasticity, dampens the ultrasonic waves which generates heat and assists in debonding the bracket Preferably, the tip is placed against the occlusal wings 32 (or occlusal side of the bracket 26). The generator 12 is activated by an appropriate switch means (not shown) so as to provide the desired frequency to piezoelectric converter 14. This in turn causes the tip 22 to vibrate in a longitudinal direction X—X at a desired amplitude A and frequency. A slight intermittent force is applied by the user against the bracket 26 until it is removed from the tooth 28. In applying the tip 22 to the work piece (for example, bracket) to be removed it is desirable that the longitudinal axis of the tool 10 be oriented such that the amplitude of movement as expressed by the longitudinal axis X—X be oriented at an acute angle with respect to the plane in which the interface between the bracket 26 and tooth 28 substantially lies. The placing of the tool at a 90° angle to the interface is extremely ineffective and would be discomforting to the patient. The longitudinal axis placed at an angle α less than about 60° and preferably less than 30°. The time typically required is within a few seconds, typically, within about one second. This is a substantial improvement over prior art magneto-restrictive devices which require up to about 30 to 40 seconds.

A device made in accordance with the present invention was used to debond orthodontic brackets 26 made of a polycrystal alumina or glass materials which were secured to a tooth 28 by commercially available adhesives, such as System 1+ and Challange Adhesives sold by Ormco Corporation and Concise and Transbond Adhesives sold by Unitek, the brackets came off within about one to two seconds leaving the adhesive on the tooth and with no apparent damage to the tooth enamel Any remaining adhesive on the tooth can be easily and quickly removed by standard deburring techniques A particular important feature of the present invention is that the debonding occurs extremely quick and is not traumatic to the patient. Furthermore, the loads necessary for bracket removal are substantially less then those required by typical removal devices.

It is to be understood that various modifications and changes can be made without departing from the scope of the present invention. For example, in the preferred embodiment illustrated, the ultrasonic dental tool 10 is used to debond orthodontic brackets from teeth, the tool 10 may also be used to fracture the interface between two other dental structures that have been secured together, for example, an orthodontic band which has been cemented to a tooth. Additionally, the present invention can also be used for fracturing other dental structures such as dental amalgams and fillings that have been secured to teeth, so long as the bond between the two dental structures is weaker than either of the components being secured together which is often the case in dental and orthodontic appliances For the purposes of the present invention, a dental structure shall be considered any component used in the dental or orthodontic field, including, but not limited to: orthodontic brackets, orthodontic bands, implants, crowns, bridges, teeth, fillings, and bones It is anticipated that the present invention would be useful in the treatment of ankylosis.

It is to be understood that various other changes and modifications may be made without the departing from the scope of the present invention For example, a separate tip may be eliminated and the outer working end of the horn can be applied directly to the bracket or other dental structure. The present invention being limited by the following claims.

We claim:

1. A method for fracturing the interface between two dental structures that have been secured together, comprising the steps:
   providing an ultrasonic device having a generator for providing a predetermined frequency, a piezoelectric converter for producing a substantially bi-directional movement along the axis of the converter at said predetermined frequency, a horn having a connecting end and a working outer end, said connecting end being secured to said converter, for transferring said bi-directional movement to said outer end of said horn; and
   placing the outer working end of said horn against one of said dental structures at an angle equal to or less than about 60° with respect to a plane substantially containing the interface between said dental structures.

2. A method according to claim 1 wherein the longitudinal axis of said device is disposed at an angle less than about 30 degrees with respect to the plane containing the interface between said dental structures.

3. A method for fracturing the interface between two dental structures that have been secured together, comprising the steps:
   providing an ultrasonic device having a converter for producing a bi-directional movement along the axis of the converter at a predetermined frequency, a horn having a connecting end and a working outer end, said connecting end being secured to said converter for transferring said bi-directional movement to said outer end of said horn; and
   placing the outer working end of said horn against one of said dental structures at an angle less than about 60° with respect to a plane containing the interface between said dental structure.

4. A method according to claim 3 wherein the longitudinal axis of said device is disposed at an angle less than about 30 degrees with respect to the plane in which the interface between said dental structures.

5. A method for fracturing the interface between two dental structures that have been secured together, comprising the steps:
   providing an ultrasonic device having a generator for providing at a frequency equal to or greater than 18 kHz, a piezoelectric converter for producing a bi-directional movement along the axis of the converter at a predetermined frequency, a horn having a connecting end and a working outer end, said connecting end being secured to said piezoelectric converter said horn transferring said bi-directional movement to said outer end of said horn, and working tip secured to the outer end of said horn, placing the tip at an acute angle with respect to the plane which substantially contains the interface between said dental structures; and
   placing the tip at an angle less than or equal to 60° with said plane containing the interface between said dental structures.

* * * * *